(12) United States Patent
Shoji et al.

(10) Patent No.: US 7,202,387 B2
(45) Date of Patent: Apr. 10, 2007

(54) PROCESS FOR PRODUCING DIMETHYL ETHER

(75) Inventors: Kazuo Shoji, Chiba (JP); Satoshi Terai, Chiba (JP)

(73) Assignee: Toyo Engineering Corporation, Tokyo (JP)

( * ) Notice: Subject to any disclaimer, the term of this patent is extended or adjusted under 35 U.S.C. 154(b) by 0 days.

(21) Appl. No.: 10/642,952

(22) Filed: Aug. 18, 2003

(65) Prior Publication Data

US 2004/0034255 A1 Feb. 19, 2004

(30) Foreign Application Priority Data

Sep. 6, 2002 (JP) ............... 2002-261828

(51) Int. Cl.
*C07C 41/09* (2006.01)
(52) U.S. Cl. ..................................... 568/698
(58) Field of Classification Search ................ 568/698
See application file for complete search history.

(56) References Cited

U.S. PATENT DOCUMENTS 4,560,807 A * 12/1985 Murai et al. ............... 568/698
4,595,785 A * 6/1986 Brake ........................ 568/698

FOREIGN PATENT DOCUMENTS

| EP | 0 124 078 A1 | 11/1984 |
| EP | 0 324 475 A1 | 7/1989 |
| JP | 49031597 A * | 3/1974 |
| JP | 59-016845 | 1/1984 |
| JP | 59-0137444 | 1/1984 |
| JP | 01-160933 | 6/1989 |
| JP | 01160933 | 6/1989 |
| JP | 02-085224 | 3/1990 |
| JP | 02085224 | 3/1990 |
| JP | 03-056433 | 3/1991 |
| JP | 03056433 | 3/1991 |

* cited by examiner

*Primary Examiner*—Rosalynd Keys
(74) *Attorney, Agent, or Firm*—Knobbe, Martens Olson & Bear LLP

(57) ABSTRACT

A process for producing dimethyl ether, which includes dehydrating methanol in vapor phase in the presence of an activated alumina catalyst having an average pore radius of 2.5 nm to 8.0 nm both inclusive and having a sodium oxide content of 0.07 wt % or less. This invention provides a process for producing DME with an improved conversion ratio using a highly active DME-production catalyst.

14 Claims, No Drawings

PROCESS FOR PRODUCING DIMETHYL ETHER

BACKGROUND OF THE INVENTION

1. Field of the Invention

This invention relates to a process for producing dimethyl ether from methyl alcohol (methanol). In particular, this invention relates to a process for producing dimethyl ether by vapor-phase dehydration of methanol in the presence of a catalyst.

2. Description of the Related Art

Dimethyl ether (DME) has been used as a propellant for spraying, and has recently attract attention as an alternative fuel to LPG or diesel oil, which does not generate particulate matters. It can be produced by, for example, direct synthesis from a synthesis gas prepared by reforming hydrocarbon materials such as methane, or dehydration of methanol.

Among these, a process for producing DME by dehydration of methanol and a catalyst used therefor have been disclosed in the references described below.

JP-A-03-056433 (1991) has disclosed a process for producing DME using a porous γ-alumina catalyst having a surface area of 210 to 300 m$^2$/g, preferably 230 to 290 m$^2$/g, a volume of pores with radius smaller than 300 Å of 0.60 to 0.90 mL/g, preferably 0.62 to 0.85 mL/g and an average pore radius of 50 to 100 Å, preferably 50 to 85 Å. This process is accomplished based on a finding that porous γ-alumina having a surface area, a pore distribution and an average pore radius in the particular ranges exhibits long-term stability. According to the examples described in this publication, a reactant is considered to be gaseous (vapor phase) methanol.

JP-A-59-016845 (1984) has disclosed a process for producing DME using an alumina catalyst having a surface area of 180 to 220 m$^2$/g, preferably 180 to 200 m$^2$/g, a pore volume 0.58 to 0.75 mL/g, preferably 0.60 to 0.75 mL/g, an average pore radius of 500 to 1000 nm, preferably 600 to 750 nm, a mode pore radius of 650 to 1000 nm, preferably 750 to 900 nm and an iron oxide (III) content of 0.5 wt % or less, preferably 0.1 wt % or less. In this technique, a pore volume of the catalyst is increased to ensure improved selectivity at a higher conversion ratio. According to the examples described in this publication, a reactant is considered to be gaseous (vapor phase) methanol.

JP-A-01-160933 (1989) has disclosed a process for producing DME wherein 5 to 45 parts by weight of steam or water is added to 100 parts by weight of methyl alcohol during vapor-phase dehydration of methyl alcohol using a γ-alumina catalyst for producing dimethyl ether. In this technique, steam or water is added to methyl alcohol in advance to considerably reduce carbon deposition on the surface of the dehydration catalyst for maintaining higher activity of the catalyst for a long term. This publication has described that a catalyst used in the process for producing DME is a γ-alumina catalyst, preferably a pure γ-alumina catalyst having lower impurity contents, i.e., 0.3% or less of silica, 0.03% or less of iron oxides and 0.10% or less of sodium oxides and having a surface area of 150 to 300 mm$^2$/g.

JP-A-02-085224 (1990) has disclosed a process for producing DME using an alumina catalyst containing at is least one metal oxide selected from Group 3A elements in the periodic table during vapor-phase dehydration of methyl alcohol for producing dimethyl ether. In this technique, an alumina catalyst containing at least one metal oxide selected from Group 3A elements in the periodic table can be used to achieve higher activity at a low temperature without carbon deposition for a long term and with formation of hydrocarbon byproducts being reduced. The publication has described that in terms of the catalyst used in the process for producing DME, a content of the metal oxide added is in the range of 0.005 to 80 wt %, preferably 0.5 to 20 wt % to the total weight of the catalyst; the pure alumina used is preferably γ-alumina having lower impurity contents, i.e., 0.3% or less of silica, 0.03% or less of iron oxides and 0.1% or less of sodium oxides and having a surface area of 100 to 700 m$^2$/g.

SUMMARY OF THE INVENTION

An objective of this invention is to provide a process for producing DME with a higher conversion ratio using a highly active DME-production catalyst consisting of activated alumina, typically γ-alumina, and using methanol as a starting material.

Another objective of this invention is to provide a process for producing DME which does not require addition of water or steam to a reaction system, and does not require addition of an active component such as a metal oxide to an activated alumina catalyst.

After intense investigation for solving the above-identified problems, the inventors have found that an average pore radius of an activated alumina catalyst, typically γ-alumina, and the amount of Na (sodium) oxide contained in the catalyst significantly affect activity and a conversion ratio in DME production, resulting in the present invention.

The present invention provides a process for producing dimethyl ether comprising dehydrating methanol in vapor phase in the presence of an activated alumina catalyst having an average pore radius of at least 2.5 nm and at most 8.0 nm and having a sodium oxide content of at most 0.07% by weight.

In the process, the activated alumina catalyst may be a γ-alumina catalyst.

Preferably, a sodium oxide content in the activated alumina catalyst is at most 0.05% by weight.

Preferably, neither water nor steam is added to the dehydration reaction system.

Preferably, no active component other than the activated alumina is added to the activated alumina catalyst.

Preferably, the dehydration is conducted at a pressure of at least 0.0 MPa-G and at most 3.0 MPa-G.

More preferably, the dehydration is conducted at a pressure of at least 1.0 MPa-G and at most 2.5 MPa-G.

DETAILED DESCRIPTION OF THE INVENTION

In an activated alumina catalyst represented by γ-alumina used in the present invention, an average pore radius is 2.5 nm to 8.0 nm both inclusive, preferably 2.5 nm to 6.7 nm both inclusive; a sodium oxide content is 0.07 wt % or less, preferably 0.05 wt % or less; and an average pore radius may be at least 2.5 nm and less than 5.0 nm. A sodium oxide content herein means a weight ratio of Na$_2$O to the amount of the catalyst where all sodium oxides contained in the catalyst are deemed to be Na$_2$O.

Herein, a specific surface area in the physical properties of a catalyst is a specific surface area determined by a BET method using nitrogen, and a pore volume is that determined by a nitrogen adsorption method. An average pore radius, a gas hourly space velocity GHSV and a conversion ratio can be calculated by formulas 1, 2 and 3, respectively.

Average pore radius=(pore volume/specific surface area)×2    Formula 1

GHSV [hour$^{-1}$]=F/V    Formula 2 wherein F represents a gas flow rate [Nm$^3$/h] and V represents a catalyst volume [m$^3$].

The unit "Nm$^3$" in a gas volume is a converted volume (cubic meter) at 0° C. and 1 atm (101 kPa).

Conversion ratio [%]=(1−(the amount of unreacted methanol/the amount of methanol fed))×100    Formula 3

Activated alumina has a large specific surface area and is active in a reaction such as decomposition, isomerization, hydrogenation, dehydrogenation and dehydration. It is, therefore, generally used as a catalyst or catalyst support. Activated alumina contains 0 to 0.5 moles of water per one mole of Al$_2$O$_3$. The content varies depending on a process temperature during heating and dehydrating alumina trihydrate which is a starting material of the activated alumina. In the course of conversion into a-alumina as anhydrous alumina by dehydration, there exist seven types of metastable aluminas, generally called as activated alumina structures, including κ-, θ-, δ, η-, χ- and ρ-alumina structures in addition to a typical γ-alumina structure (Publication Department, Kaken Research Center Management Development Center "Novel High Performance Adsorbents (Experimental Data Collection)", p. 361, published on Apr. 5, 1976).

Activated alumina is generally prepared by extracting alumina from an alumina-rich mineral such as bauxite, kaoline, acid white clay and colloidal clay; converting the alumina into alumina hydrate by hydrolysis or neutralization; and then activating the hydrate.

In a Bayer process, the most typical process of the industrial preparation processes for alumina, bauxite as a starting material is ground and the resultant powder is treated with a hot solution of sodium hydroxide to elute alumina as sodium aluminate, during which the substantially whole amounts of impurities such as iron oxides, silica and titanium oxide are separated as an insoluble residue. If there exists alkali-soluble silica, it reacts with alkali and alumina to form an alkali aluminosilicate hydrate which is insoluble. The residue is removed by filtration and the filtrate, a sodium aluminate solution, is appropriately diluted. To the solution, a seed of gibbsite, which is crystalline alumina trihydrate, is added at an appropriate temperature. While stirring the mixture, aluminum hydroxide is precipitated. The precipitate is collected by filtration, washed with water and dried to give sodium-rich alumina trihydrate (gibbsite). The alumina trihydrate can be heated and dehydrated to give various activated aluminas containing 0 to 0.5 moles of water per 1 mole of Al$_2$O$_3$ (Publication Department, Kaken Research Center Management Development Center "Novel High Performance Adsorbents (Experimental Data Collection)", p. 371, published on Apr. 5, 1976).

Although activated alumina thus obtained contains silica and iron oxides as impurities derived from a starting mineral up to about 0.1 to 0.02 wt %, such a level does not affect dehydration in the present invention. Rather, residual sodium added during refinement of the starting mineral affects reaction activity. Sodium oxides are required to be removed to a level of at least 0.07 wt % or less, preferably 0.05 wt % or less on the basis of Na$_2$O.

Activated alumina is generally used as a catalyst after shaping. It can be shaped by various methods such as shaping aluminum hydroxide; forming hydrosol of basic aluminum sulfate or aluminum chloride from an aqueous solution of aluminum sulfate or aluminum chloride and then adding it dropwise into an oil to form spheres; or hydrolyzing an aqueous solution of an aluminum salt to give hydrogel, which is then shaped into a desired form. Activated alumina thus shaped can be heated and dehydrated to give an activated alumina catalyst.

An activated alumina catalyst may have a shape of sphere, cylinder or pellet, but may have any other common shape for a catalyst. Alternatively, it may have a honeycomb construction or plate form.

An example of a high purity alumina as a starting material for a γ-alumina catalyst is CATAPAL B (Brand Name) available from CONDEA Ltd. It is preferable to wash γ-alumina with an acid for reducing the amount of sodium oxides in the γ-alumina catalyst. However, as long as an average pore radius described below can be achieved and the amount of sodium oxides can be reduced, any other known technique may be applied than acid-washing. In order to reduce sodium oxides content in the catalyst, it is possible to remove sodium oxides from the starting material or from the shaped catalyst. Acid-washing may be conducted at an appropriate stage, depending on the type or production process of a starting γ-alumina and a level of removing sodium oxides. The content of sodium oxides in an activated alumina catalyst other than a γ-alumina catalyst may be similarly reduced, for example, by washing with an acid.

An average pore radius is calculated based on a ratio of a pore volume to a specific surface area, and is generally known to be controllable by adjusting the size of starting particles and a temperature of heat treatment. The inventors have found that when a sodium oxide content in an activated alumina catalyst is within the above particular range, excellent catalyst activity can be achieved by controlling an average pore radius within a particular range, resulting in this invention.

When an average pore radius is 2.5 nm to 8.0 nm both inclusive, preferably 2.5 nm to 6.7 nm both inclusive, and a sodium oxide content is more than 0.07 wt %, a conversion ratio may be lower. Furthermore, when a sodium oxide content is 0.07 wt % or less, preferably 0.05 wt % or less, and an average pore radius is less than 2.5 nm or more than 8.0 nm, a conversion ratio is also lower.

In a vapor phase reaction using a solid catalyst, when a pore size is smaller in relation to molecular sizes of a reactant and a product, a diffusion resistance generally tends to be larger, leading to a lower reaction efficiency. When a pore size is larger in relation to molecular sizes of a reactant and a product, the number of active sites within a catalyst tends to be fewer, leading to a lower reaction efficiency. Thus, there exists an optimal pore size range for a reaction system. When a pore size is within the optimal range, a larger specific surface area is preferable because of the larger number of active sites.

A specific surface area in activated alumina is generally about 100 to 400 m$^2$/g. In case that an average pore radius is 2.5 nm to 8.0 nm both inclusive, for example, a pore volume range is 0.125 to 0.4 mL/g when a specific surface area is 100 m$^2$/g, and a pore volume range is 0.5 to 1.6 mL/g when a specific surface area is 400 m$^2$/g. A catalyst in which a specific surface area and a pore volume are within these ranges may be suitably used in the present invention.

During dehydration of methanol in the presence of an activated alumina catalyst for producing DME, a reaction temperature is preferably 350° C. or less, more preferably 330° C. or less in the light of inhibiting byproduct formation, while being preferably 250° C. or more, more preferably 280° C. or more in the light of a reaction rate. A gas hourly space velocity (GHSV) is preferably 900 h$^{-1}$ or more, more preferably 1000 h$^{-1}$ or more, further preferably 1500 h$^{-1}$ or more in the light of preventing an economical efficiency in DME production from being reduced due to an excessive amount of a catalyst, while being preferably 4000 h$^{-1}$ or less, more preferably 3000 h$^{-1}$ or less in the light of preventing a conversion ratio of methanol from being lowered due to a short reaction time. In the light of kinetics, a lower reaction pressure is advantageous. Thus, a reaction pressure for the dehydration of methanol is preferably 3.0 MPa-G (gauge pressure) or less, more preferably 2.5 MPa-G or less. On the other hand, in the light of collection of DME produced, a higher pressure is preferable. Thus, a reaction pressure is preferably 0 MPa-G or more, more preferably 1.0 MPa-G or more. Specifically, DME produced may be condensed by cooling and collected by gas-liquid separation. Thus, the use of a refrigerator may be required for condensation at a lower reaction pressure while cooling water or an air cooler may be used for condensation at a higher reaction pressure. A high pressure such that necessity for using a refrigerator can be eliminated is, therefore, desirable in the light of both cost for plant construction and energy consumption, particularly in large scale production. A catalyst used in the present invention can exhibit higher activity in a DME production reaction even at such a higher pressure.

A starting methanol is preferably equivalent to, but not limited to, Grade AA (99.85 wt %) methanol described in the US Federal Specification O-M-232J.

Journal of the Japan Petroleum Institute, 45, (3), 169–174, 2002 has shown that in dehydration of methanol for producing dimethyl ether, addition of water or steam tends to reduce a partial pressure of methanol, leading to reduction in a reaction rate. In the present invention, such addition of water or steam is not necessary and in the light of a conversion ratio of methanol, it is preferable not to add water or steam.

Even using high purity methanol substantially free from water as a starting material, an equivalent amount of H$_2$O is produced as a DME production reaction proceeds. A large amount of steam, therefore, presents in a lower part of a catalyst layer. A catalyst used in the present invention can exhibit excellent activity even under such conditions, and can be suitably used when a starting material is low purity methanol containing water.

It is known to add (support, blend, etc.) an active component to an alumina catalyst for dimethyl ether production. Known examples of such an active component include oxides of Group 3 metals in the periodic table such as yttrium and lanthanum. In the present invention, it is not necessary for an activated alumina catalyst to further comprise an active component other than the activated alumina (hereinafter, referred to as "additional active component"). Rather, it is preferable to use a catalyst containing no additional active components in the light of an economic efficiency because addition (supporting, blending, etc.) of an additional active component leads to an additional cost. Herein, "an activated alumina catalyst containing no additional active components" includes an activated alumina catalyst containing an additional active component to an extent that it does not affect catalyst activity. For example, when an additional active component is contained in a catalyst as an impurity, it is not necessary to remove the impurity.

EXAMPLES

The present invention will be more specifically described with reference to several non-limiting examples, in which starting methanol has a purity equivalent to a special grade chemical (99.8% or higher).

A sodium oxide content in a catalyst was determined by photoelectro-photometric emission spectrometry of JIS K0116. Specifically, a sample is calicined, pulverized and then quantitatively analyzed as Na$_2$O by photoelectro-photometric emission spectrometry (JIS K0116) using GQM-75 (Shimadzu Corporation). Products were analyzed by gas chromatography (Agilent Technology Inc., Type G2890A).

No additional active component is added to the catalysts used in examples below.

Example 1

Five (5) mL of a γ-alumina catalyst having a specific surface area of 115 m$^2$/g, a pore volume of 0.37 mL/g, an average pore radius of 6.48 nm and a Na$_2$O content of 0.02 wt % was loaded in a stainless fixed bed reactor with an inner diameter of 16 mm equipped with an electric furnace around its periphery.

Then, at a reaction temperature of 300° C., methanol was fed at a GHSV of 1700 h$^{-1}$ and a pressure of 1.1 MPa-G (gauge pressure), while methanol was heated to its evaporating temperature at the reaction pressure in an upstream line of the reactor so that methanol was vaporized before entering the catalyst layer.

During the process, a temperature of the catalyst layer was 300° C. A conversion ratio of methanol to DME was 75% under these conditions. The results are shown in Table 1.

Example 2

A reaction was conducted in the same manner as described in Example 1, except that 5 mL of a γ-alumina catalyst having a specific surface area of 240 m$^2$/g, a pore volume of 0.75 mL/g, an average pore radius of 6.25 nm and a Na$_2$O content of 0.04 wt % was loaded.

A conversion ratio of methanol to DME was 75% under these conditions. The results are shown in Table 1.

Example 3

A reaction was conducted in the same manner as described in Example 1, except that 5 mL of a γ-alumina catalyst having a specific surface area of 252 m$^2$/g, a pore volume of 0.45 mL/g, an average pore radius of 3.58 nm and a Na$_2$O content of 0.002 wt % was loaded, a reaction pressure was 0.0 MPa-G (gauge pressure) and a temperature of the catalyst layer was 290° C.

A conversion ratio of methanol to DME was 87% under these conditions. The results are shown in Table 1.

Example 4

A reaction was conducted in the same manner as described in Example 3, except that a reaction pressure was 1.1 MPa-G (gauge pressure) and a temperature of the catalyst layer was 300° C.

A conversion ratio of methanol to DME was 77% under these conditions. The results are shown in Table 1.

Example 5

A reaction was conducted in the same manner as described in Example 3, except that a reaction pressure was 2.0 MPa-G (gauge pressure) and a temperature of the catalyst layer was 300° C.

A conversion ratio of methanol to DME was 70% under these conditions. The results are shown in Table 1.

Example 6

A reaction was conducted in the same manner as described in Example 3, except that a reaction pressure was 3.0 MPa-G (gauge pressure) and a temperature of the catalyst layer was 310° C.

A conversion ratio of methanol to DME was 72% under these conditions. The results are shown in Table 1.

Comparative Example 1

A reaction was conducted in the same manner as described in Example 1, except that 5 mL of a γ-alumina catalyst having a specific surface area of 117 $m^2/g$, a pore volume of 0.35 mL/g, an average pore radius of 6.05 nm and a $Na_2O$ content of 0.25 wt % was loaded.

A conversion ratio of methanol to DME was 41% under these conditions. The results are shown in Table 1.

Comparative Example 2

A reaction was conducted in the same manner as described in Example 1, except that 5 mL of a γ-alumina catalyst having a specific surface area of 206 $m^2/g$, a pore volume of 0.31 mL/g, an average pore radius of 3.00 nm and a $Na_2O$ content of 0.25 wt % was loaded.

A conversion ratio of methanol to DME was 28% under these conditions. The results are shown in Table 1.

Comparative Example 3

A reaction was conducted in the same manner as described in Example 1, except that 5 mL of a γ-alumina catalyst having a specific surface area of 146 $m^2/g$, a pore volume of 0.71 mL/g, an average pore radius of 9.73 nm and a $Na_2O$ content of 0.04 wt % was packed.

A conversion ratio of methanol to DME was 57% under these conditions. The results are shown in Table 1.

Comparative Example 4

A reaction was conducted in the same manner as described in Example 1, except that 2.2 g (5 mL) of a γ-alumina catalyst having a specific surface area of 165 $m^2/g$, a pore volume of 0.20 mL/g, an average pore radius of 2.42 nm and a $Na_2O$ content of 0.02 wt % was loaded.

A conversion ratio of methanol to DME was 48% under these conditions. The results are shown in Table 1.

As described above, the present invention can provide a process for producing DME from methanol as a starting material with an improved conversion ratio, using a highly active DME-production catalyst consisting of activated alumina without the necessity for adding an additional active component.

Numerous modifications and variations of the present invention are possible in light of the above teachings. It is therefore to be understood that within the scope of the appended claims,ingredients the invention may be practiced otherwise than as specifically described herein.

TABLE 1

| Run | $Na_2O$ (wt %) | Specific surface area ($m^2/g$) | Pore volume (mL/g) | Average pore radius (nm) | Pressure (MPa · G) | Temperature (° C.) | GHSV ($h^{-1}$) | Conversion ratio (%) | $SiO_2$ (wt %) | $Fe_2O_2$ (wt %) |
|---|---|---|---|---|---|---|---|---|---|---|
| Example 1 | 0.02 | 115 | 0.37 | 6.48 | 1.1 | 300 | 1700 | 75 | 0.02 | 0.02 |
| Example 2 | 0.04 | 240 | 0.75 | 6.25 | 1.1 | 300 | 1700 | 75 | 0.06 | 0.04 |
| Example 3 | 0.002 | 252 | 0.45 | 3.58 | 0.0 | 290 | 1700 | 87 | 0.02 | 0.015 |
| Example 4 | 0.002 | 252 | 0.45 | 3.58 | 1.1 | 300 | 1700 | 77 | 0.02 | 0.015 |
| Example 5 | 0.002 | 252 | 0.45 | 3.58 | 2.0 | 300 | 1700 | 70 | 0.02 | 0.015 |
| Example 6 | 0.002 | 252 | 0.45 | 3.58 | 3.0 | 310 | 1700 | 72 | 0.02 | 0.015 |
| Comp. Exam. 1 | 0.25 | 117 | 0.35 | 6.05 | 1.1 | 300 | 1700 | 41 | 0.02 | 0.02 |
| Comp. Exam. 2 | 0.25 | 206 | 0.31 | 3.00 | 1.1 | 300 | 1700 | 28 | 0.02 | 0.02 |
| Comp. Exam. 3 | 0.04 | 146 | 0.71 | 9.73 | 1.1 | 300 | 1700 | 57 | 0.06 | 0.04 |
| Comp. Exam. 4 | 0.02 | 165 | 0.20 | 2.42 | 1.1 | 300 | 1700 | 48 | 0.06 | 0.04 |

*In a product, no components other than DME, water or unreacted methanol were detected.

What is claimed is:

1. A method for producing dimethyl ether comprising:
   obtaining an activated alumina catalyst by using as criteria its sodium oxide content and its average pore radius, wherein the sodium oxide content is 0.07% by weight or less and the average pore radius is no less than 2.5 nm but less than 5.0 nm, said activated alumina catalyst having a pore volume of no less than 0.125 mL/g but no more than 0.45 mL/g; and
   dehydrating methanol in vapor phase in the presence of the activated alumina catalyst, wherein no active component other than the activated alumina is added to the activated alumina catalyst, thereby producing dimethyl ether.

2. The method according to claim 1, wherein the activated alumina catalyst is a γ-alumina catalyst.

3. The method according to claim 1, wherein the sodium oxide content in the activated alumina catalyst is at most 0.05% by weight.

4. The method according to claim 1, wherein the sodium oxide content in the activated alumina catalyst is at most 0.04% by weight.

5. The method according to claim 1, wherein neither water nor steam is added in the dehydration step.

6. The method according to claim 1, wherein the dehydration is conducted at a pressure of at least 0.0 MPa-G and at most 3.0 MPa-G.

7. The method according to claim 1, wherein the dehydration is conducted at a pressure of at least 1.0 MPa-G and at most 2.5 MPa-G.

8. A method for producing dimethyl ether comprising:
providing an activated alumina catalyst having a sodium oxide content of 0.07% by weight or less, an average pore radius of no less than 2.5 nm but less than 5.0 nm, and a pore volume of no less than 0.125 mL/g but no more than 0.45 mL/g; and
dehydrating methanol in vapor phase in the presence of the activated alumina catalyst wherein no active component other than the activated alumina is added to the activated alumina catalyst, thereby producing dimethyl ether wherein production of dimethyl ether is increased, when the sodium oxide content is within the aforesaid range, by controlling the average pore radius of the activated alumina catalyst.

9. The method according to claim 8, wherein the activated alumina catalyst is a γ-alumina catalyst.

10. The method according to claim 8, wherein the sodium oxide content in the activated alumina catalyst is at most 0.05% by weight.

11. The method according to claim 8, wherein the sodium oxide content in the activated alumina catalyst is at most 0.04% by weight.

12. The method according to claim 8, wherein neither water nor steam is added in the dehydration step.

13. The method according to claim 8, wherein the dehydration is conducted at a pressure of at least 0.0 MPa-G and at most 3.0 MPa-G.

14. The method according to claim 8, wherein the dehydration is conducted at a pressure of at least 1.0 MPa-G and at most 2.5 MPa-G.

* * * * *